United States Patent [19]

Steinmetz

[11] 4,419,529

[45] Dec. 6, 1983

[54] PROCESS FOR THE PREPARATION OF A 2-ALKYLPHENOL

[75] Inventor: Arthur Steinmetz, Seelze, Fed. Rep. of Germany

[73] Assignee: Riedel-de Haen Aktiengesellschaft, Seelze, Fed. Rep. of Germany

[21] Appl. No.: 354,308

[22] Filed: Mar. 3, 1982

[30] Foreign Application Priority Data

Mar. 5, 1981 [DE] Fed. Rep. of Germany ....... 3108265

[51] Int. Cl.³ ..................... C07C 37/00; C07C 39/06
[52] U.S. Cl. .................................. 568/772; 568/774; 568/799; 568/782; 568/780
[58] Field of Search ............... 568/772, 780, 774, 799, 568/744, 782

[56] References Cited

U.S. PATENT DOCUMENTS

| | | | |
|---|---|---|---|
| 2,723,659 | 11/1955 | Young et al. | 126/360 |
| 2,732,300 | 11/1955 | Beute | 122/235 |
| 2,909,568 | 10/1959 | Gleim | 568/799 |
| 4,098,139 | 7/1978 | Sankey | 74/410 |

FOREIGN PATENT DOCUMENTS

| | | | |
|---|---|---|---|
| 118272 | 2/1976 | Fed. Rep. of Germany | 568/763 |
| 2716036 | 4/1977 | Fed. Rep. of Germany | 568/799 |
| 2610374 | 9/1977 | Fed. Rep. of Germany | 568/772 |

OTHER PUBLICATIONS

William, "J. Organic Chemistry", vol. 22, Jul.–Dec. 1957, pp. 772–773.
Houben-Weyl, *Methoden der Organischen Chemie*, vol. V/1a, Part 1 (1970), pp. 268–269.

*Primary Examiner*—Werren B. Lone
*Attorney, Agent, or Firm*—Curtis, Morris & Safford

[57] ABSTRACT

A 2-alkylphenol is prepared by reduction of a 2-acylphenol in the presence of a metallic catalyst. The reaction is carried out at a temperature of 80° to 200° C. and under a pressure of 10 to 100 bars, and a base metal, in particular copper, is used as a catalyst. It is particularly advantageous to use the catalyst in combination with a support. The hydrogenation of the acylphenol is advantageously carried out in the presence of an inert solvent. The process can be carried out continuously or discontinuously. The alkylphenols obtained are suitable for use in the synthesis of active substances having biocidal properties.

15 Claims, No Drawings

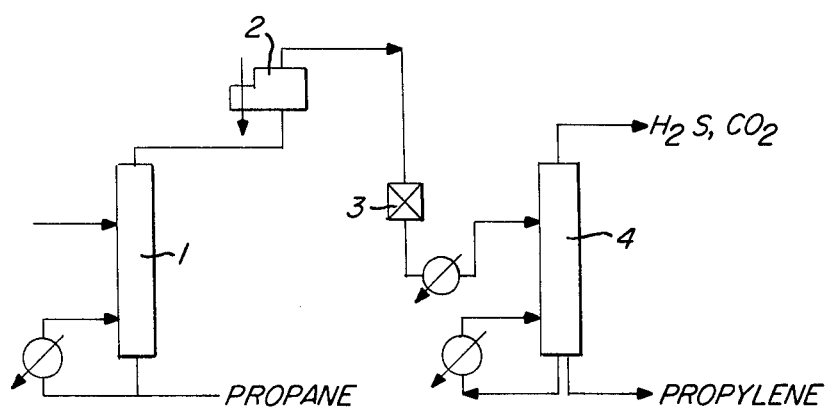

PROCESS FOR THE PREPARATION OF A 2-ALKYLPHENOL

The invention relates to a process for the preparation of a 2-alkylphenol by reduction of a 2-acylphenol in the presence of a metallic catalyst.

It is known that certain alkylphenols can be prepared by reduction of the corresponding acylphenols with the aid of hydrogen in the presence of metallic catalysts. Thus, for example, the hydrogenation of acylhydroquinone has been carried out with the use of palladium-on-carbon (cf. U.S. Pat. Nos. 2,728,659 and 2,732,300), and 4,6-diethylresorcinol has been obtained by hydrogenation of 4,6-diacetylresorcinol in the presence of a nickel catalyst, in particular Raney nickel, within a limited temperature range (cf. German Offenlegungsschrift No. 2,610,374). Noble metal catalysts such as palladium cannot be employed universally for reasons of cost, and Raney nickel can be used only to a limited extent since it frequently brings about at the same time nuclear hydrogenation.

The object of the invention is to provide a process for the catalytic hydrogenation of 2-acylphenols, which is more generally applicable and can be carried out to any desired extent, and which is effective with inexpensive metal catalysts and produces high yields.

The invention thus relates to a process for the preparation of a 2-alkylphenol by reduction of a 2-acylphenol in the presence of a metalic catalyst, which process comprises hydrogenating a 2-acylphenol at a temperature of 80° to 200° C. and under a pressure of 10 to 100 bars, if desired in the presence of an inert solvent, in the presence of a catalytically effective amount of a base metal.

A particularly suitable starting material for the process according to the invention is a 2-acylphenol of the formula (1)

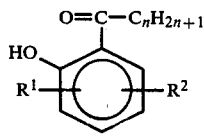

in which n represents an integer from 2 to 17, preferably from 3 to 7, and $R^1$ and $R^2$ are identical or different and each denote a hydrogen atom, a halogen atom, such as preferably a chlorine or bromine atom, a hydroxyl group, an alkoxy group having 1 to 16, preferably 1 to 12, carbon atoms, an acyl or acyloxy group each having 2 to 10, preferably 4 to 8, carbon atoms, a dialkylamino group having a total of 2 to 14, preferably 2 to 8, carbon atoms or a hydrocarbon radical having 1 to 16, preferably 1 to 12, carbon atoms, which hydrocarbon radical is above all an alkyl radical, a phenyl radical or an alkylphenyl radical.

The hydrogenation according to the invention of 2-acylphenols to give 2-alkylphenols is carried out at a temperature of 80° to 200° C., preferably 100° to 160° C.; a reaction temperature of 135° to 150° C. is particularly advantageous. The reaction is carried out in the presence of gaseous hydrogen under a pressure of 10 to 100 bars, preferably 20 to 60 bars, the range from 30 to 50 bars being the most advantageous.

It is advisable to carry out the reaction in the presence of a solvent which is inert to the reactants. The solvent, which can also be a mixture of various liquids, is employed, depending on the particular case, in an amount of 50 to 2,000, preferably 100 to 1,000, percent by weight, an amount of 200 to 400 percent by weight being particularly advantageous (relative to the 2-acylphenol). Particularly suitable solvents are monohydric or dihydric alkanols having 1 to 4 carbon atoms, for example methanol, ethanol, 1-propanol, 2-propanol, 1-butanol, 2-butanol, 2-methylpropan-1-ol, 2-methylpropan-2-ol, 1,2-ethanediol and 1,2-propanediol. Also suitable are aprotic solvents, in particular ethers, such as 1,2-dimethoxyethane, tetrahydrofuran or 1,4-dioxane, saturated carboxylic acid esters, such as ethyl acetate, and aromatic hydrocarbons, such as benzene, toluene or xylene, and also water.

It is an essential feature of the process according to the invention that the hydrogenation is carried out in the presence of a catalytically effective amount of a base metal. The base metal is used in an amount of 1 to 25, preferably 2 to 15 percent by weight, and an amount of 5 to 10 percent by weight is particularly preferred (relative to the 2-acylphenol). A suitable base metal is in particular copper but also nickel or cobalt, depending on the substitution of the 2-acylphenol.

A preferred embodiment of the process comprises using a base metal fixed on a support as a catalyst. The weight ratio of the base metal to support is here 1:0.2 to 1:10, preferably 1:0.5 to 1:2. This embodiment has the advantage that it is possible to work up the reaction mixture in a particularly simple manner. Suitable support materials are oxides, for example silicon dioxide, magnesium oxide, aluminium oxide, titanium dioxide, zirconium oxide and thorium oxide, further silicates, for example chrysotile, actinolite and crocidolite, and also aluminates, for example corundum and bauxite. Of these, silicon dioxide (diatomaceous earth) and aluminium oxide (alumina) are preferred.

The process according to the invention can be carried out continuously or discontinuously. The starting material, the catalyst and, if desired, the solvent are usually initially introduced into an autoclave equipped with a mixing tool, for example a stirrer. The autoclave is then flushed to remove atmospheric oxygen by means of an inert gas, preferably nitrogen, and filled with hydrogen. The mixture is then heated to the reaction temperature and maintained at the reaction temperature with constant agitation, preferably by means of stirring, and with a constant supply of hydrogen, until no more hydrogen is being taken up. After the reaction mixture has been cooled to a temperature below the boiling point of the solvent used, in the case of reactions which do not use a solvent above the melting point of the acylphenol, preferably within the range from 40° to 60° C., the solids are separated off, preferably by means of filtration; the solvent if used is then removed, preferably by evaporation, and the reaction product is isolated and purified. The degree of purity is determined by gas chromatography; it is at least 92%, preferably at least 98%. The yield is in general at least 90%, preferably at least 95%, of theory (relative to a pure product).

2-alkylphenols obtained according to the invention are suitable for use in the synthesis of active substances having biocidal properties; they are also used for the preparation of pharmaceutical formulations and also of preservatives and disinfectants.

The examples below illustrate the invention. Percentage data are in each case data by weight.

EXAMPLE 1

200 g of 2-caproylphenol, 800 ml of ethanol and 20 g of a commercially available copper catalyst, which contained 60% of copper on a silicon dioxide support, were initially introduced into a 2 liter stirred autoclave. The autoclave was flushed with nitrogen and then filled with hydrogen up to a pressure of 20 bars. The autoclave contents were heated for 90 minutes at 150° C., during which period the hydrogen pressure was maintained at about 35 bars. The reaction mixture was then cooled to 60° C. and filtered, and the filtrate was concentrated under a pressure of 20 mbars. 182 g (=98.1% of theory) of 2-hexylphenol, which was 95.1% pure, were obtained. After distillation under a pressure of 10 mbars and at a temperature of 130° to 132° C., a colorless product was obtained.

EXAMPLE 2

Example 1 was repeated using 4-butanoylresorcinol as the starting material and methanol as the solvent, the reaction time being 70 minutes and the hydrogen pressure 40 bars. 186 g (=100% of theory) of 4-butylresorcinol, which was 95.8% pure, were obtained. After distillation under a pressure of 10 mbars and at a temperature of 166° to 168° C., a colorless, crystallizing product having a melting point of 47° to 48° C. was obtained.

EXAMPLE 3

Example 1 was repeated using 4-(2-ethylcaproyl)-resorcinol as the starting material and methanol as the solvent, the reaction time being 100 minutes. 188 g (=99.8% of theory) of (±)-4-(2-ethylhexyl)-resorcinol, which was 99.2% pure, were obtained. After distillation under a pressure of 10 mbars and at a temperature of 182° to 185° C., a colorless, crystallizing product having a melting point of 48° to 50° C. was obtained.

I claim:

1. A process for the preparation of a 2-alkylphenol by reduction of a 2-acylphenol in the presence of a metallic catalyst, which comprises hydrogenating 2-acylphenol of the formula

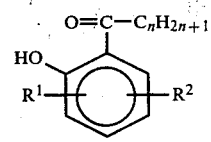

in which n represents an integer from 2 to 17 and $R^1$ and $R^2$ are identical or different and each denote a hydrogen atom, a halogen atom, a hydroxyl group, an alkoxy group having 1 to 16 carbon atoms, an acyl or acyloxy group each having 2 to 10 carbon atoms, a dialkylamino group having a total of 2 to 14 carbon atoms or a hydrocarbon radical having 1 to 16 carbon atoms, at a temperature of 80° to 200° C. and in the presence of gaseous hydrogen under a pressure of 10 to 100 bars and in the presence of a catalytically effective amount of a base metal selected from the group consisting of copper, nickel and cobalt.

2. The process of claim 1, wherein said base metal is fixed on a suitable catalyst support.

3. The process of claim 2, wherein the weight ratio of said base metal to the support is 1:0.2 to 1:10.

4. The process of claim 2, wherein the weight ratio of said base metal to the support is 1:0.5 to 1:2.

5. The process of claim 1, wherein said base metal is used in an amount of 1 to 25 percent by weight relative to said acylphenol.

6. The process of claim 1, wherein said base metal is used in an amount of 2 to 15 percent by weight relative to said acylphenol.

7. The process of claim 1, wherein said base metal is used in an amount of 5 to 10 percent by weight relative to said acylphenol.

8. The process of claim 1, wherein said hydrogenation is carried out in the presence of an inert solvent.

9. The process of claim 8, wherein said solvent is used in an amount of 50 to 2,000 percent by weight relative to said acylphenol.

10. The process of claim 8, wherein said solvent is used in an amount of 100 to 1,000 percent by weight relative to said acylphenol.

11. The process of claim 1, wherein said solvent is used in an amount of 200 to 400 percent by weight relative to said acylphenol.

12. The process of claim 1, wherein said temperature is 100° to 160° C.

13. The process of claim 1, wherein said temperature is 135° to 150° C.

14. The process of claim 1, wherein said pressure is 20 to 60 bars.

15. The process of claim 1, wherein said pressure is 30 to 50 bars.

* * * * *